United States Patent
Remmers et al.

[11] Patent Number: 5,826,579
[45] Date of Patent: Oct. 27, 1998

[54] REMOTE-CONTROLLED MANDIBULAR POSITIONING DEVICE AND METHOD OF USING THE DEVICE

[75] Inventors: John E. Remmers; Eric A. Hajduk; Ronald S. Platt, all of Calgary; Alan A. Lowe, Vancouver, all of Canada

[73] Assignee: University Technologies International, Inc., Calgary, Canada

[21] Appl. No.: 736,900

[22] Filed: Oct. 25, 1996

Related U.S. Application Data

[60] Provisional application No. 60/007,155, Nov. 1, 1995.
[51] Int. Cl.$^6$ .................................................. A61F 5/56
[52] U.S. Cl. .......................................................... 128/848
[58] Field of Search .......................... 128/848, 859–862, 128/323, 534–536, 544–546

[56] References Cited

U.S. PATENT DOCUMENTS

| | | | |
|---|---|---|---|
| 4,304,227 | 12/1981 | Samelson | 128/136 |
| 4,368,041 | 1/1983 | Roup | 433/69 |
| 4,593,686 | 6/1986 | Lloyd et al. | 128/136 |
| 4,830,008 | 5/1989 | Meer | 128/421 |
| 5,313,960 | 5/1994 | Tomasi | 128/848 |
| 5,340,309 | 8/1994 | Robertson | 433/69 |
| 5,365,945 | 11/1994 | Halstrom | 128/848 |
| 5,409,017 | 4/1995 | Lowe | 128/848 |
| 5,427,117 | 6/1995 | Thornton | 128/848 |
| 5,467,783 | 11/1995 | Meade | 128/848 |
| 5,499,633 | 3/1996 | Fenton | 128/848 |
| 5,536,168 | 7/1996 | Bourke | 433/6 |
| 5,537,994 | 7/1996 | Thornton | 128/204.18 |
| 5,537,997 | 7/1996 | Mechlenburg et al. | 128/204.23 |
| 5,540,219 | 7/1996 | Mechlenburg et al. | 128/204.23 |
| 5,540,733 | 7/1996 | Testerman et al. | 607/42 |
| 5,562,106 | 10/1996 | Heeke et al. | 128/848 |
| 5,678,567 | 10/1997 | Thornton et al. | 128/848 |

*Primary Examiner*—Francis J. Jaworski
*Attorney, Agent, or Firm*—Burns, Doane, Swecker & Mathis, L.L.P.

[57] ABSTRACT

A remote-controlled mandibular positioner for conveniently and precisely positioning the mandible during a sleep center or in-hospital study of patients who are candidates for mandibular positioner therapy. The remote-controlled mandibular positioner is used during sleep to perform a therapeutic titration study during full polysomnographic monitoring to determine the mandible position effective in treating obstructive sleep apnea. During the titration study, the mandible is advanced by a technician using the remote-controlled mandibular positioner until all apneas and hypopneas are eliminated. The titration study determines whether a mandibular positioner will be effective in treating a particular patient, and if so, the degree of mandibular ventral displacement required for effective treatment of obstructive sleep apnea.

31 Claims, 13 Drawing Sheets

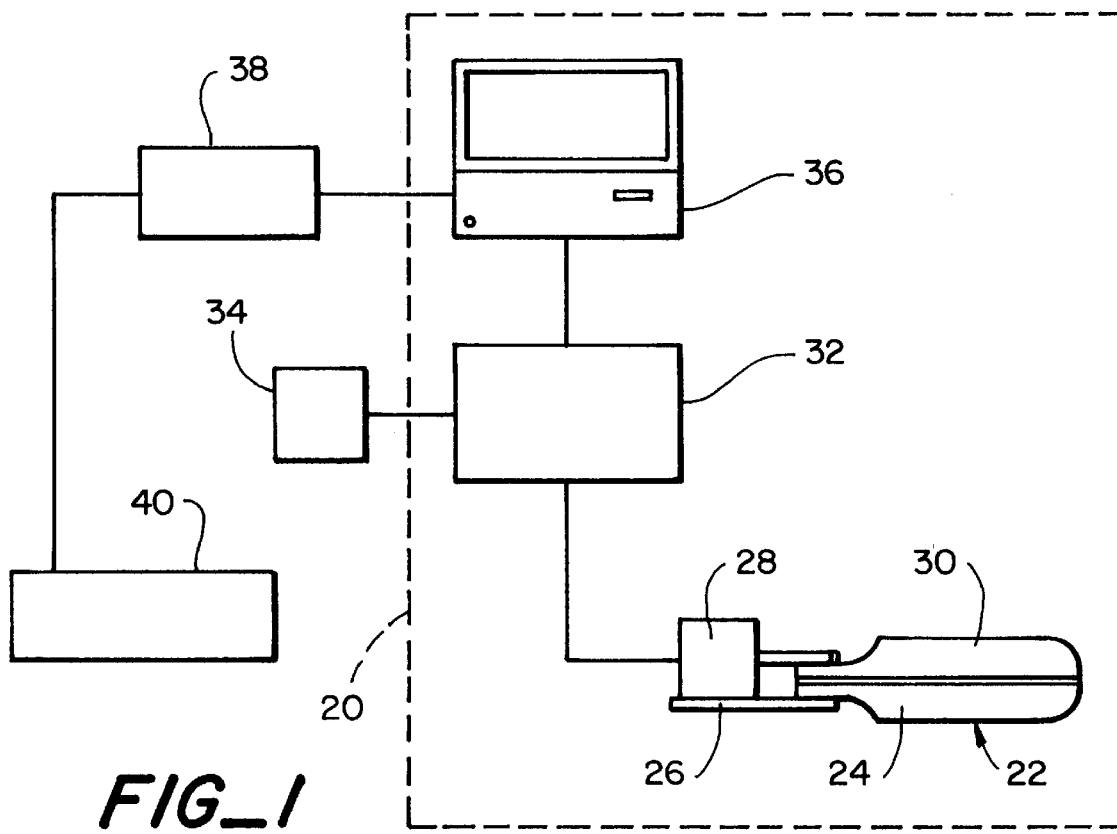
FIG_1
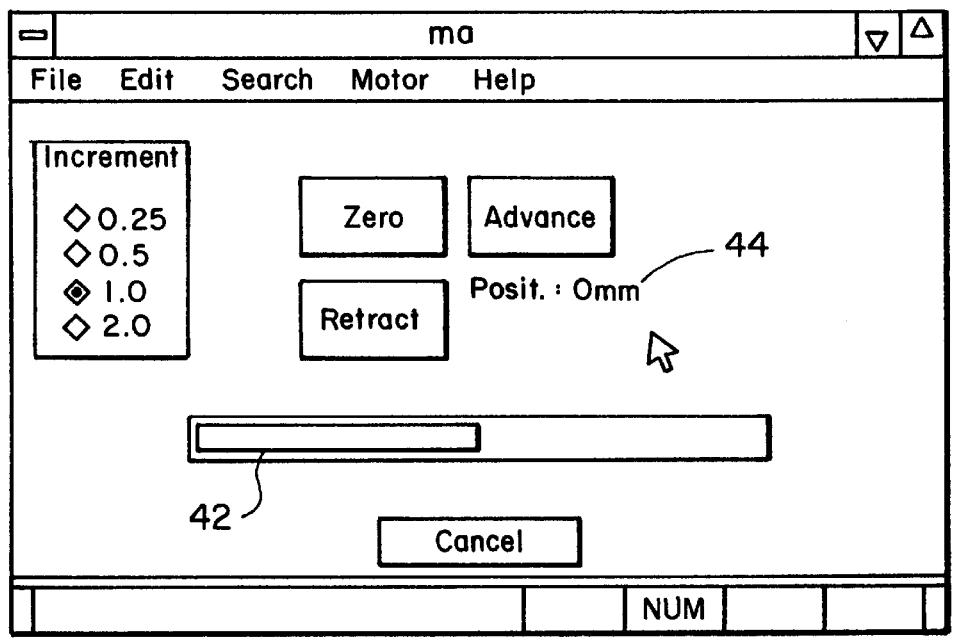
FIG_2

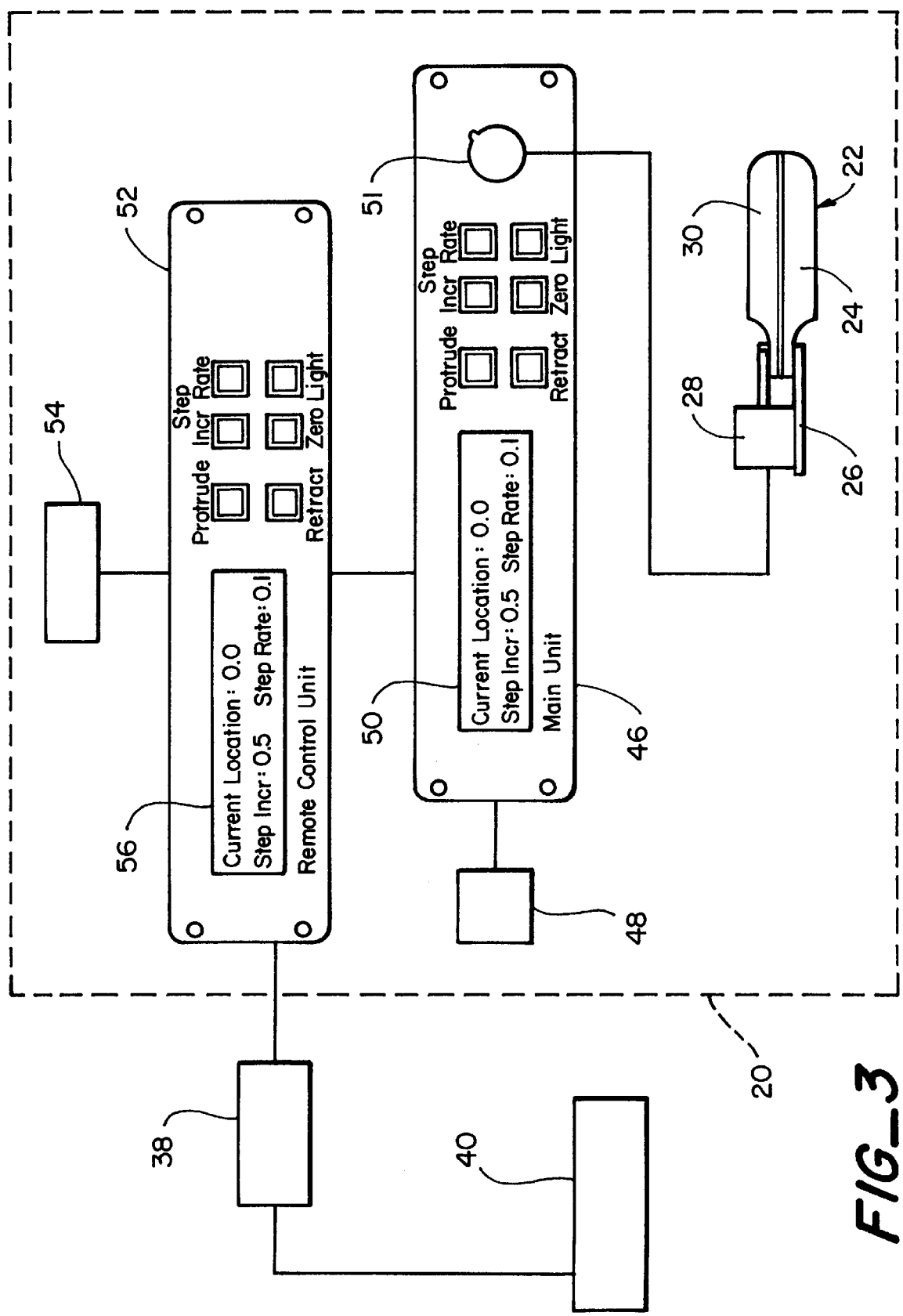
FIG_3

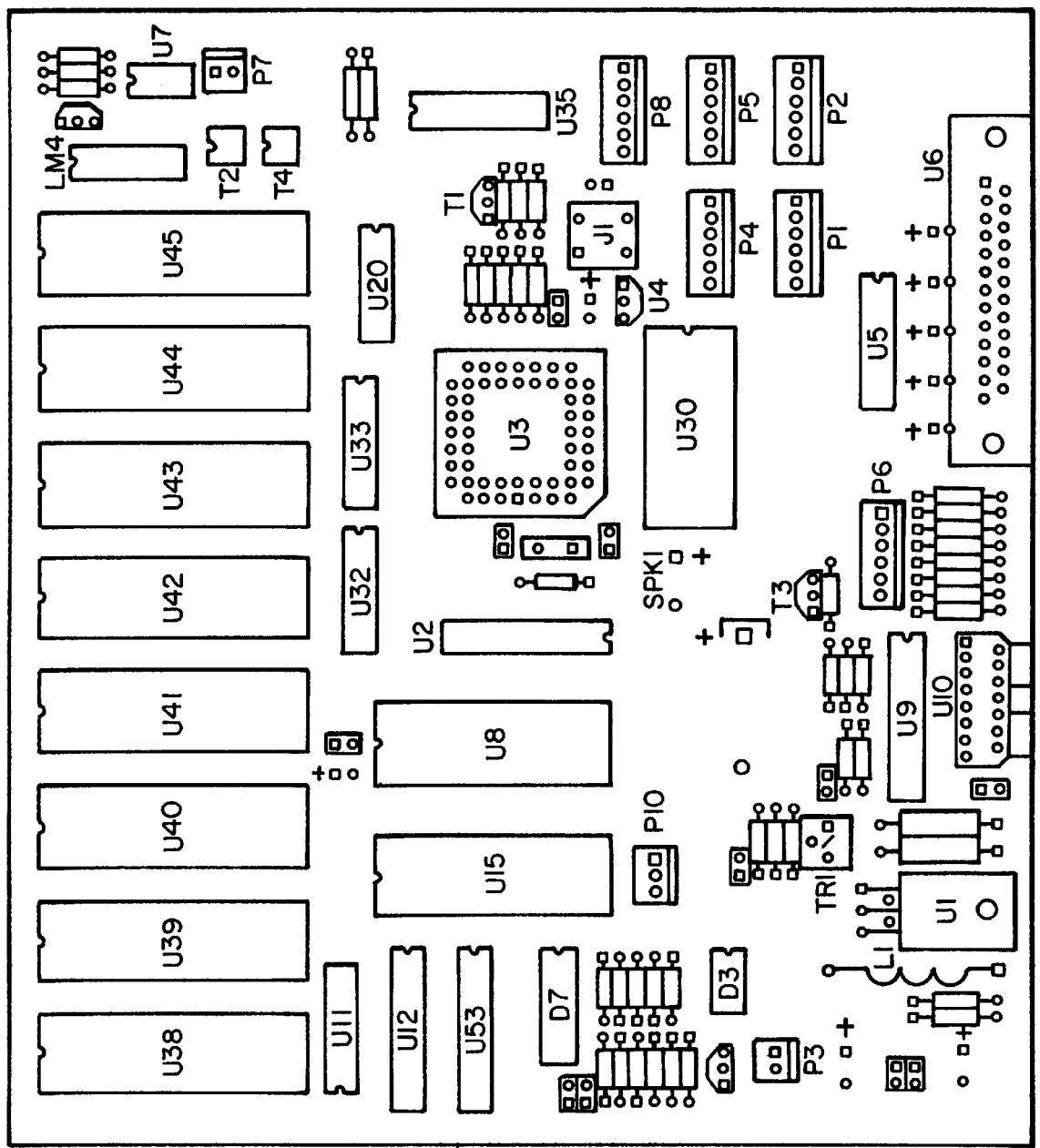
FIG_4

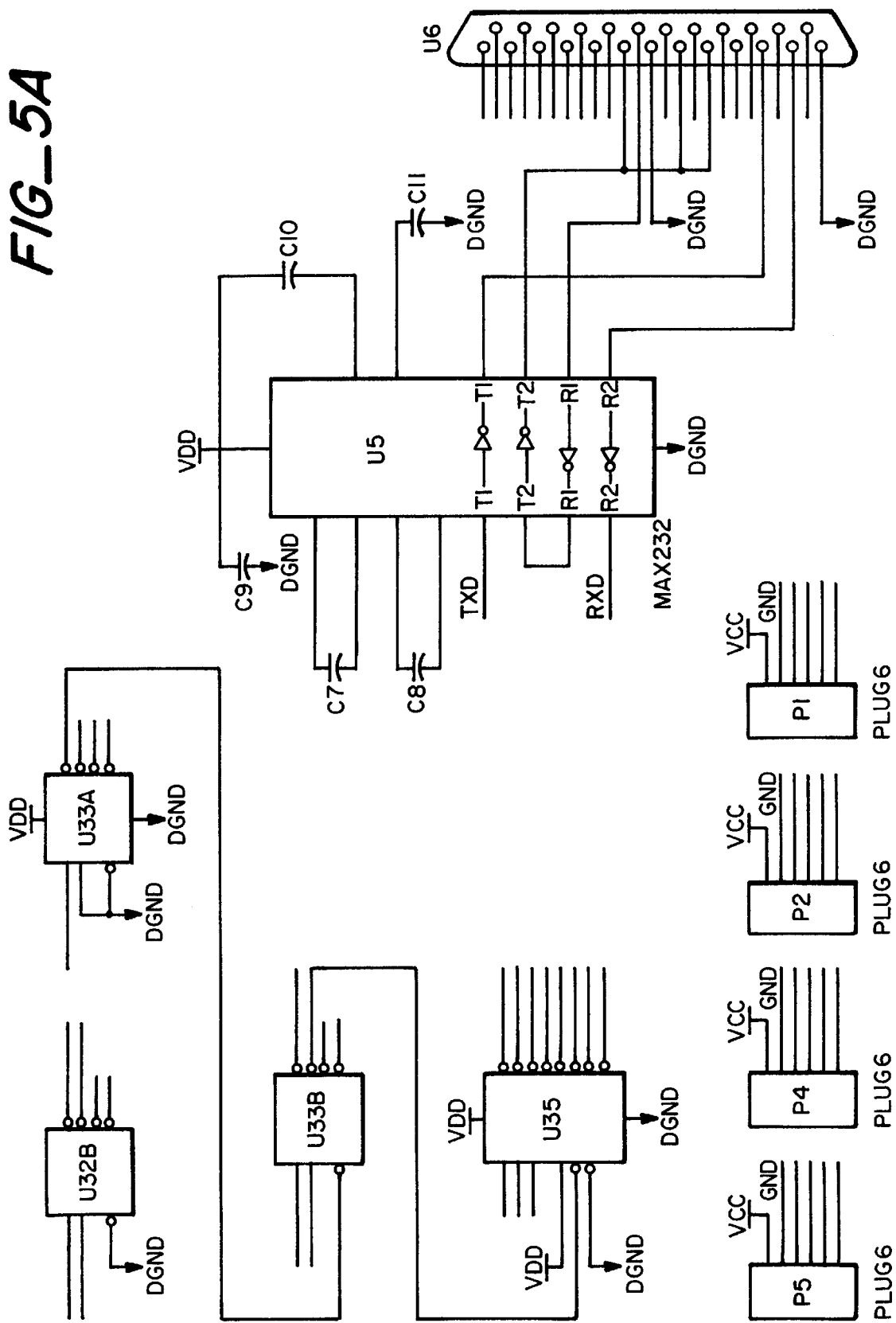

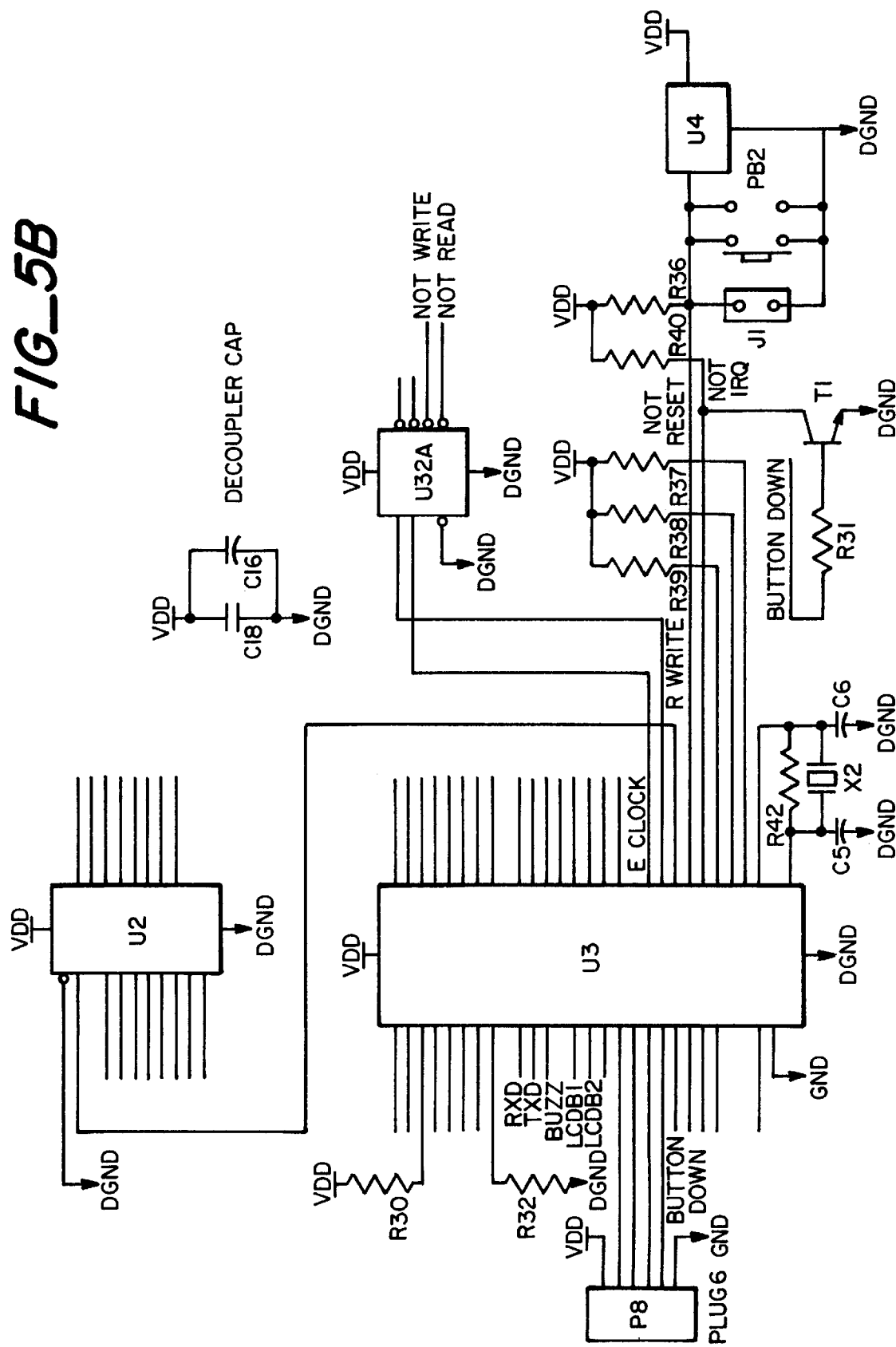
FIG_5B

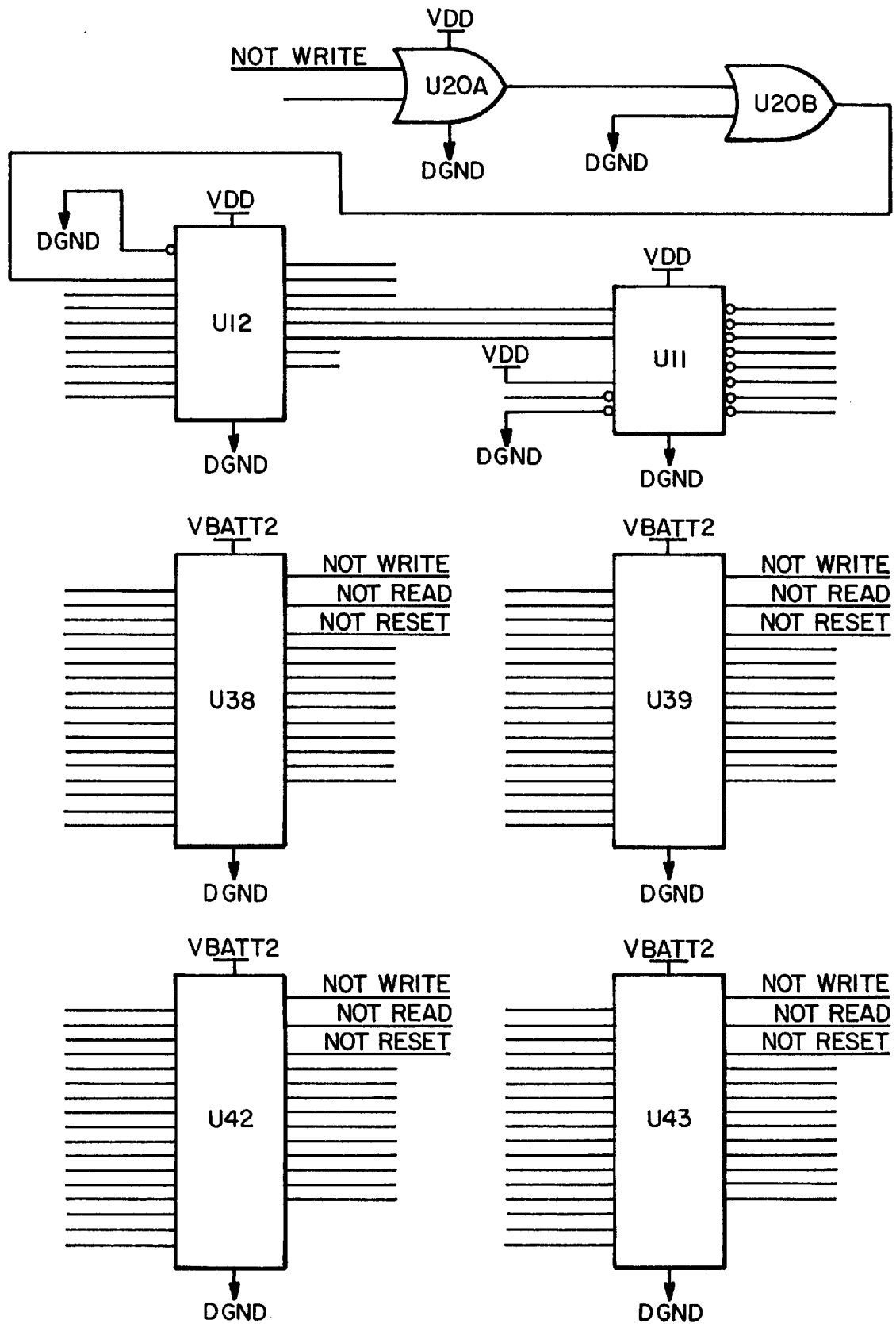
FIG_6A

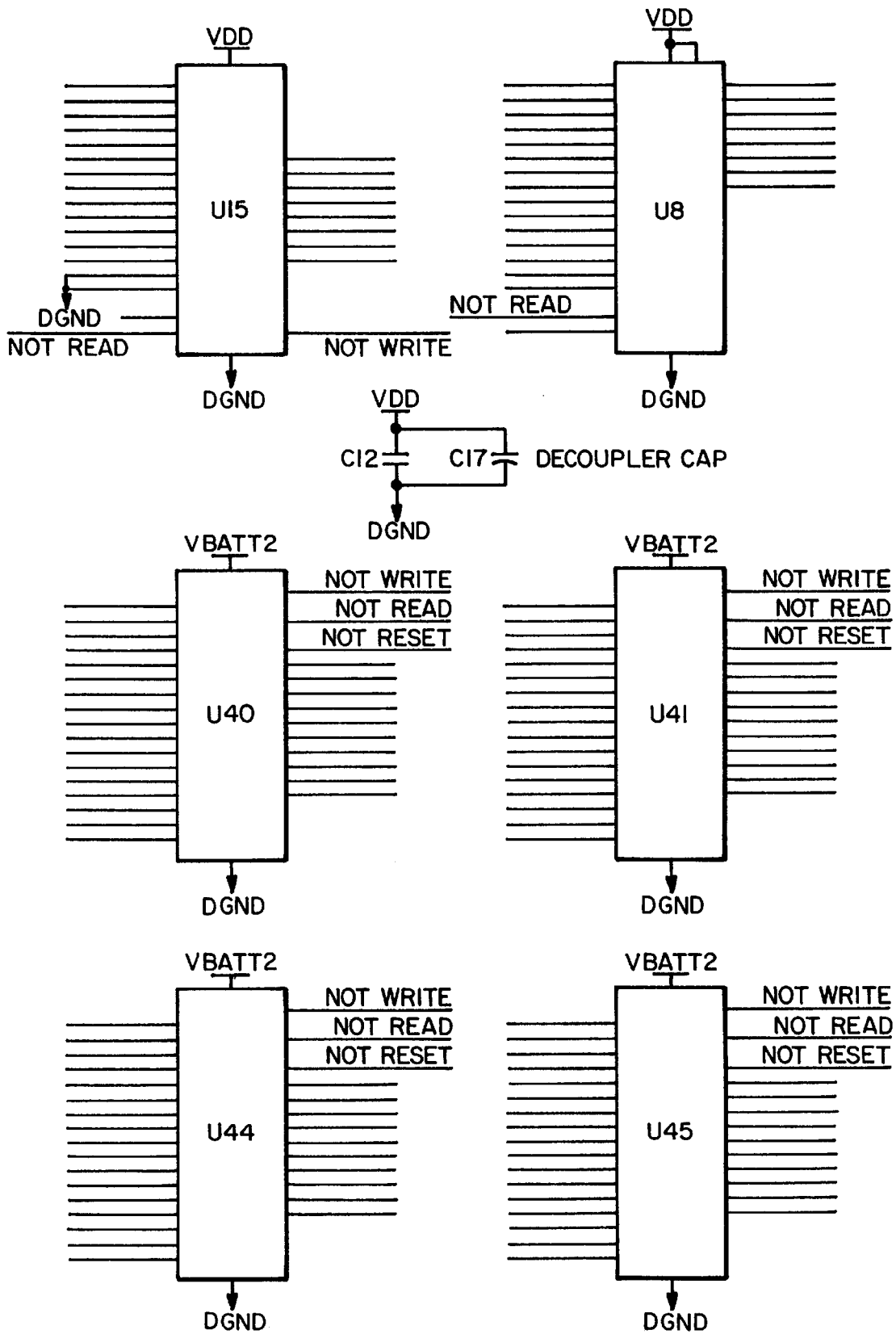
FIG_6B

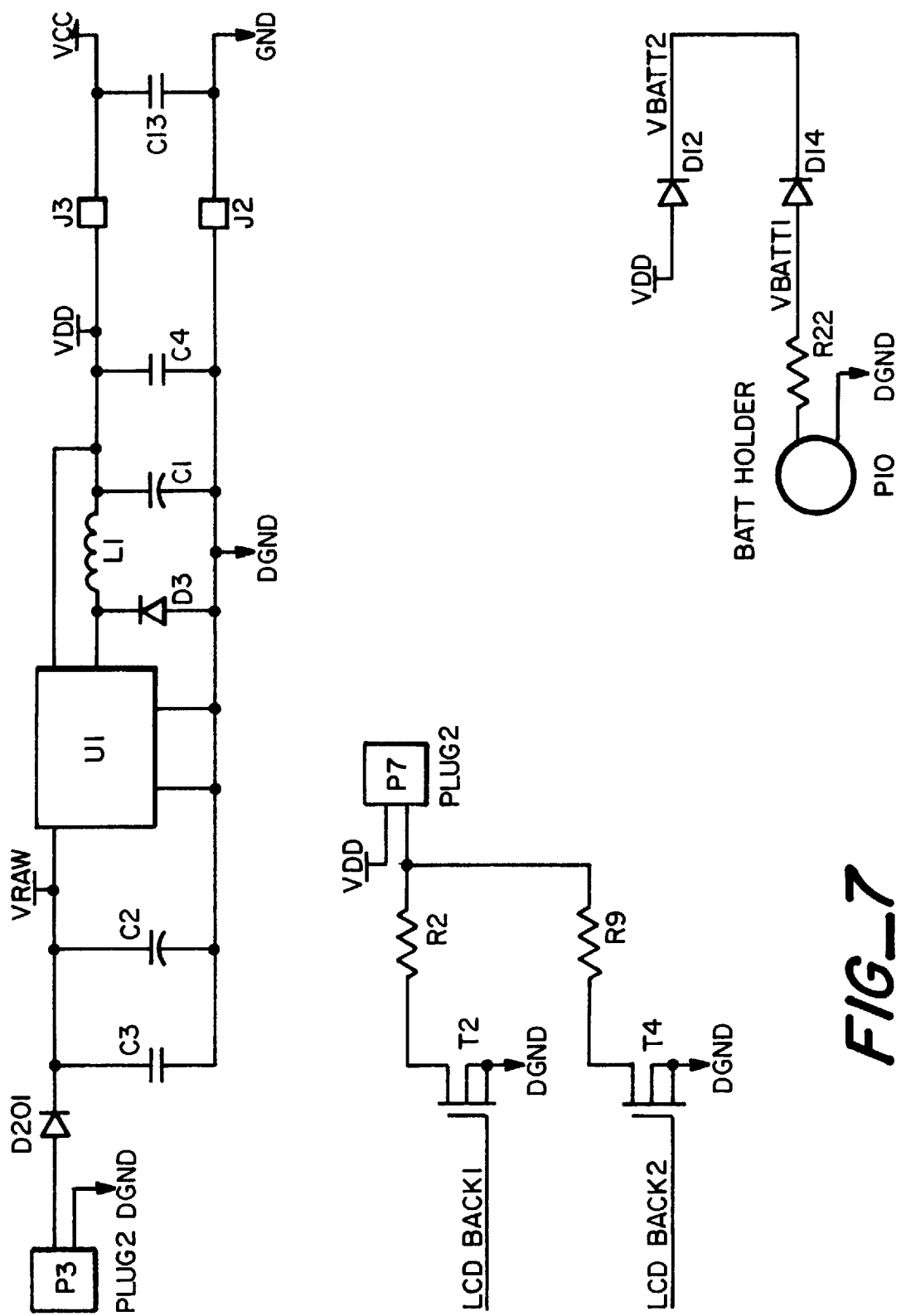
FIG_7

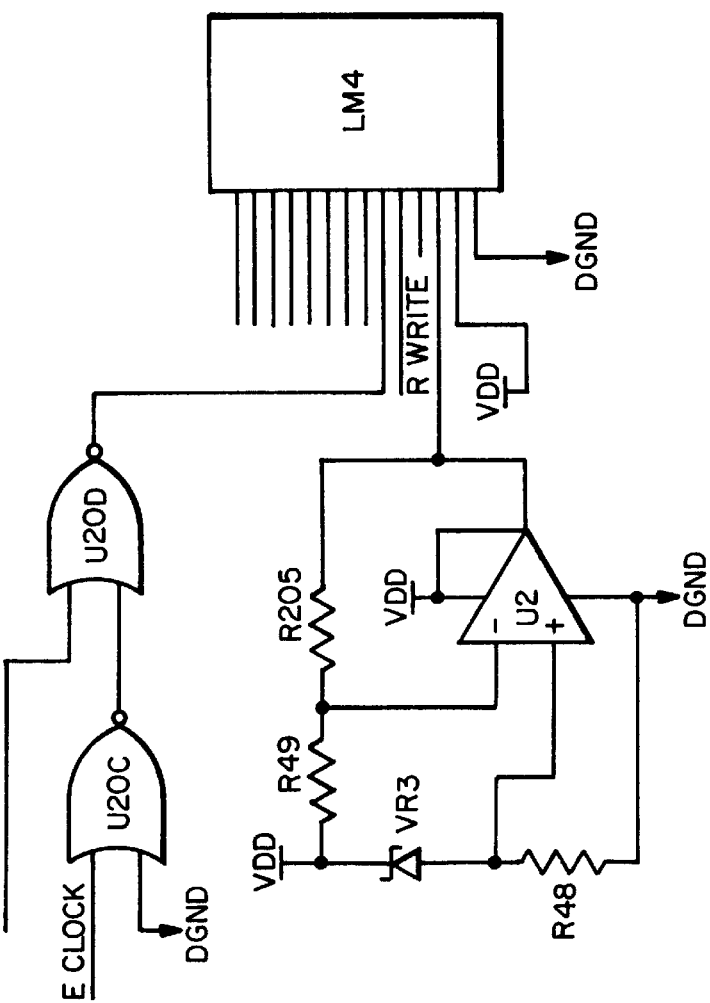
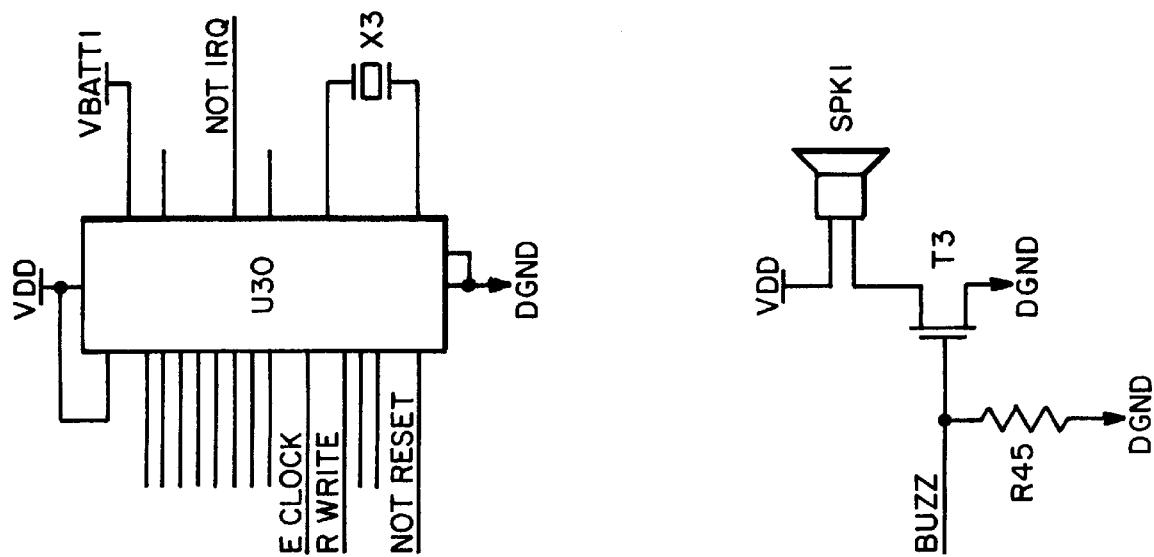
FIG_8

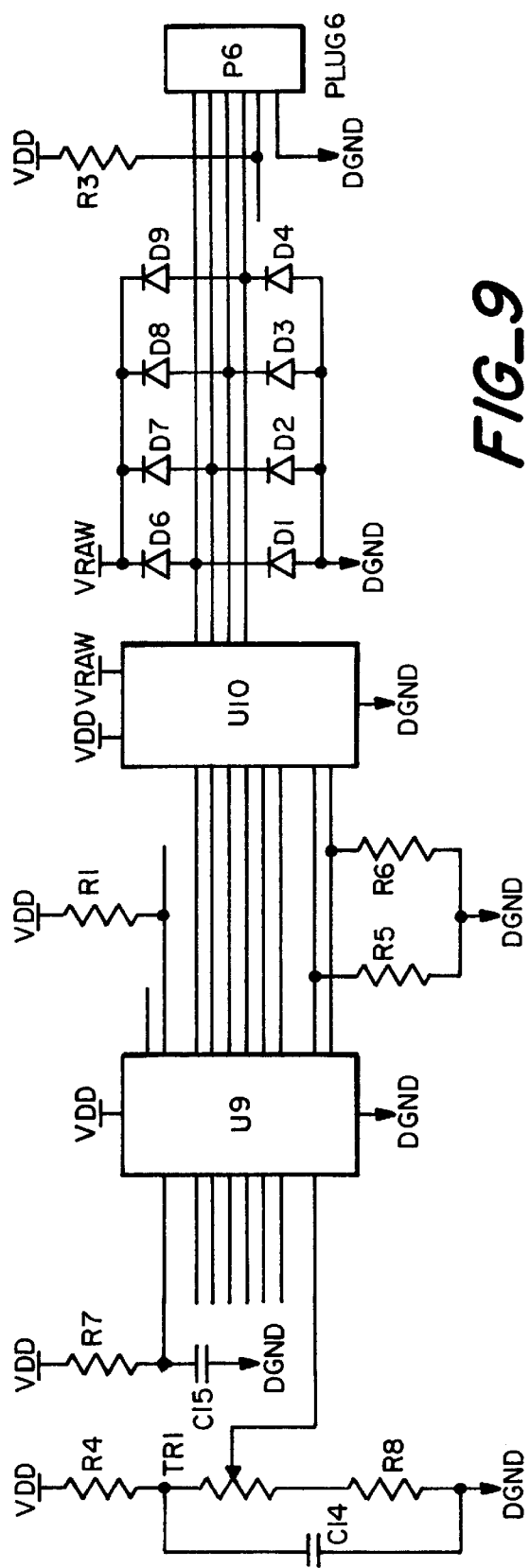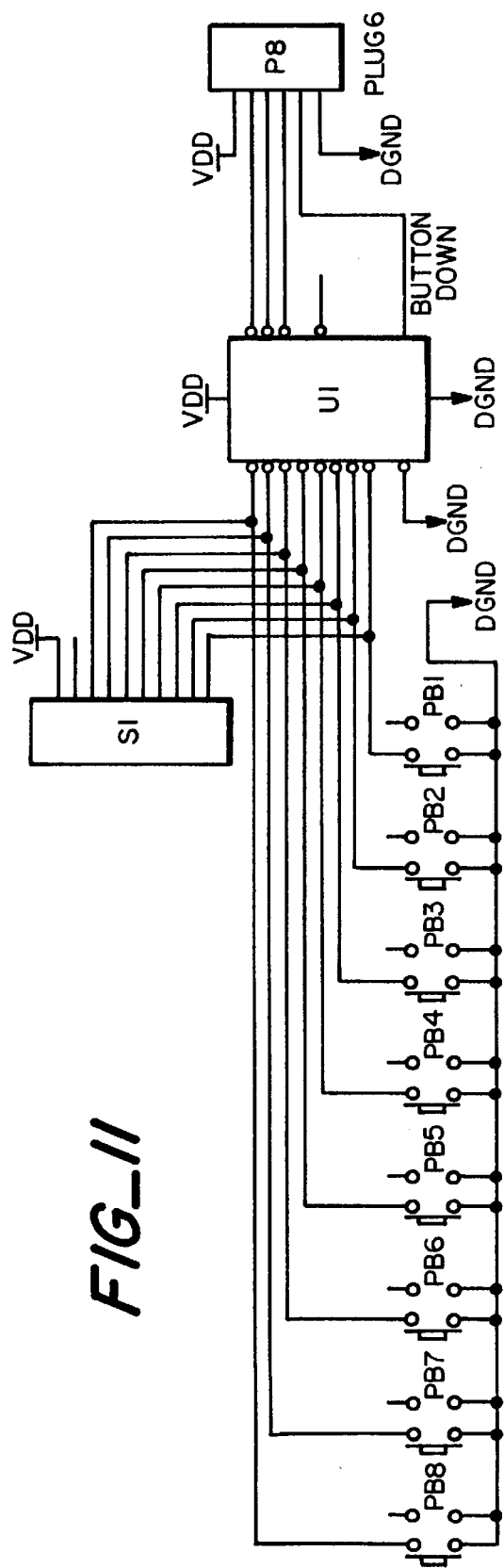
FIG_9
FIG_11

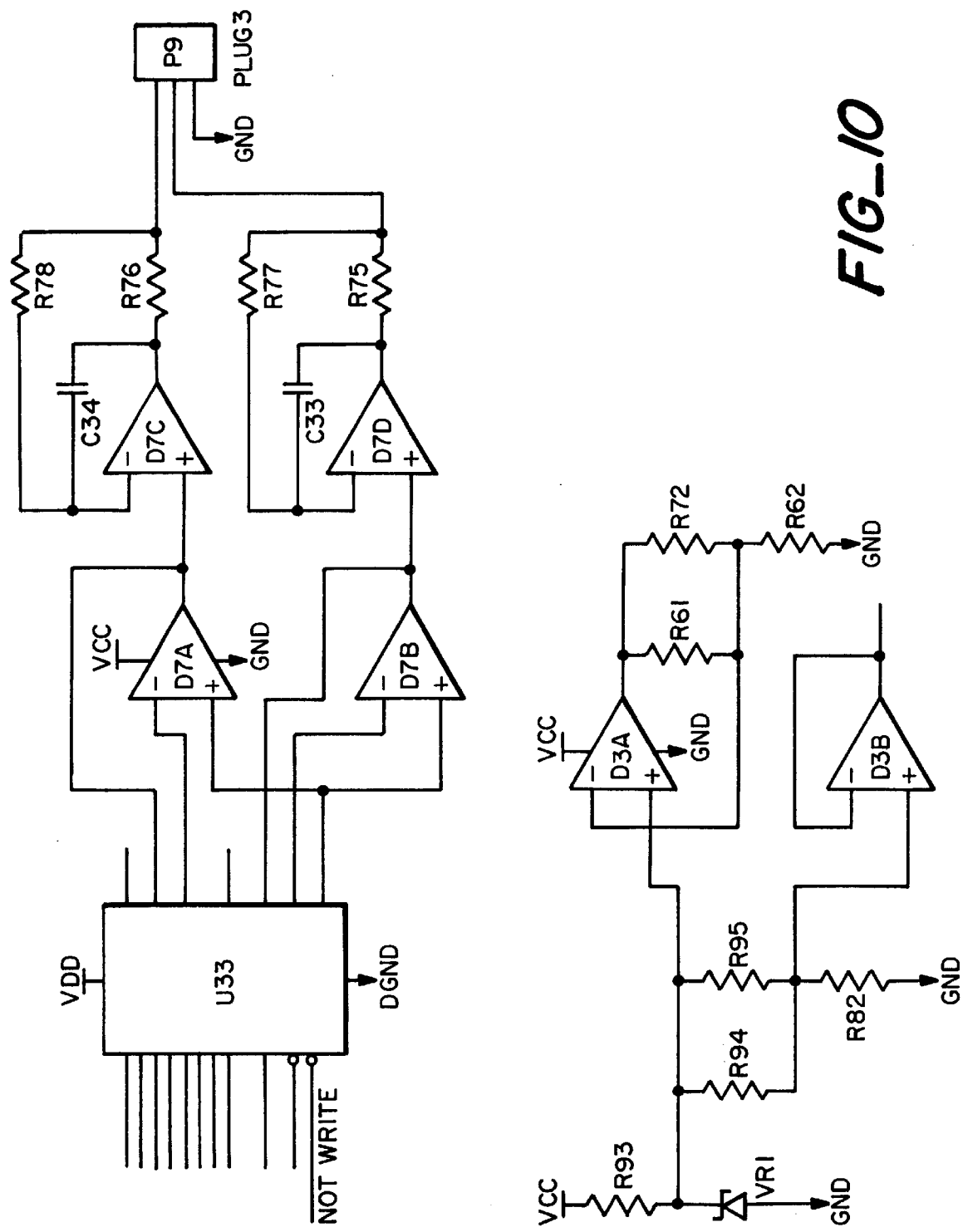
FIG_10

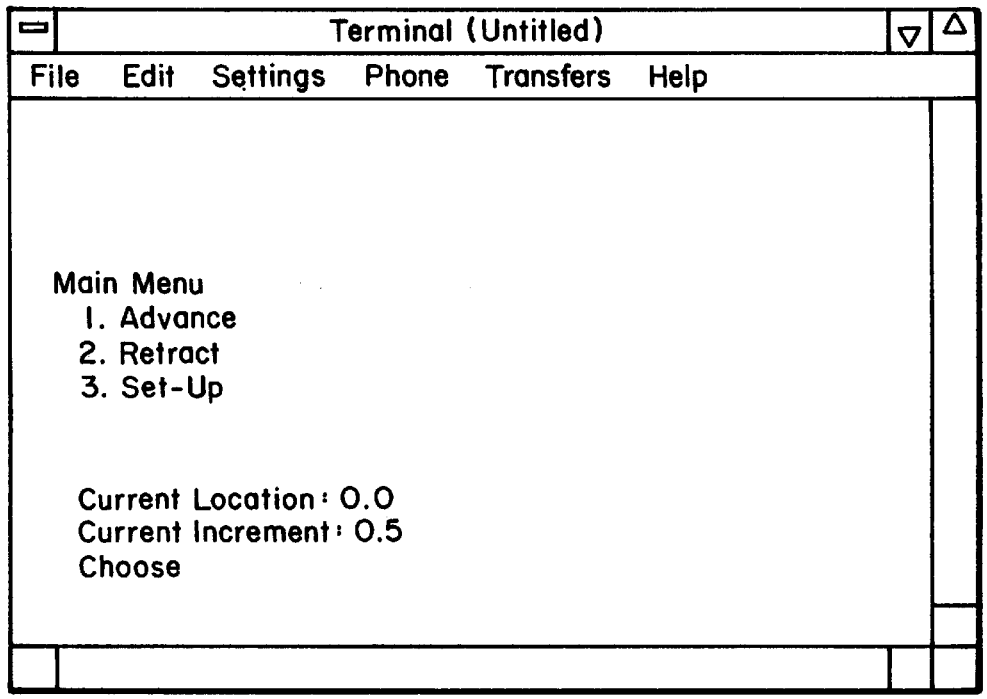
FIG_12
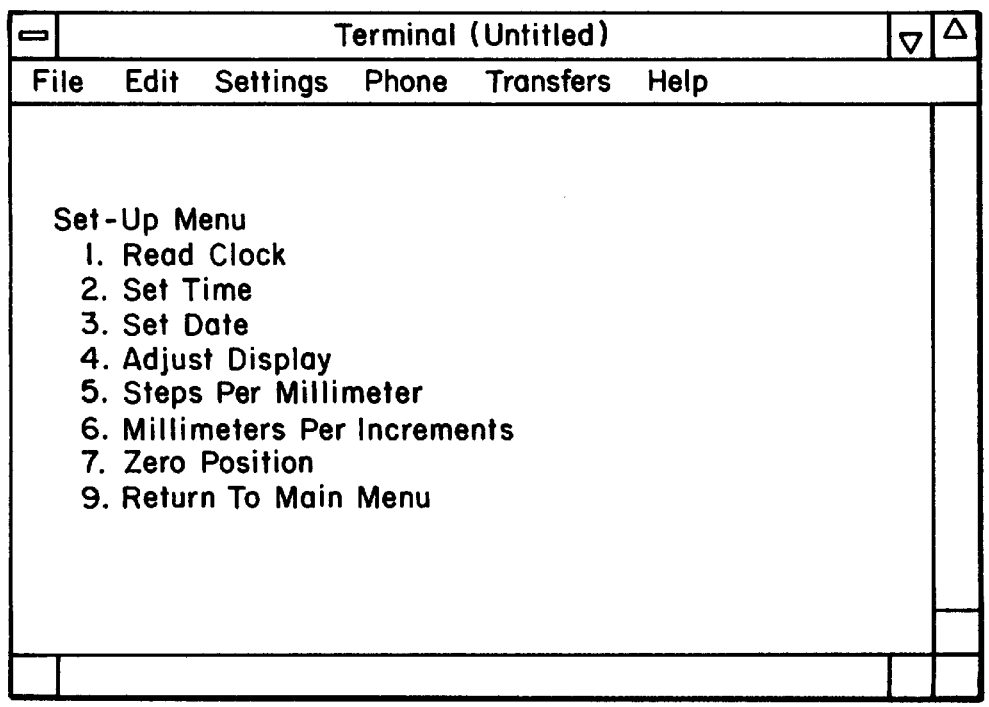
FIG_13

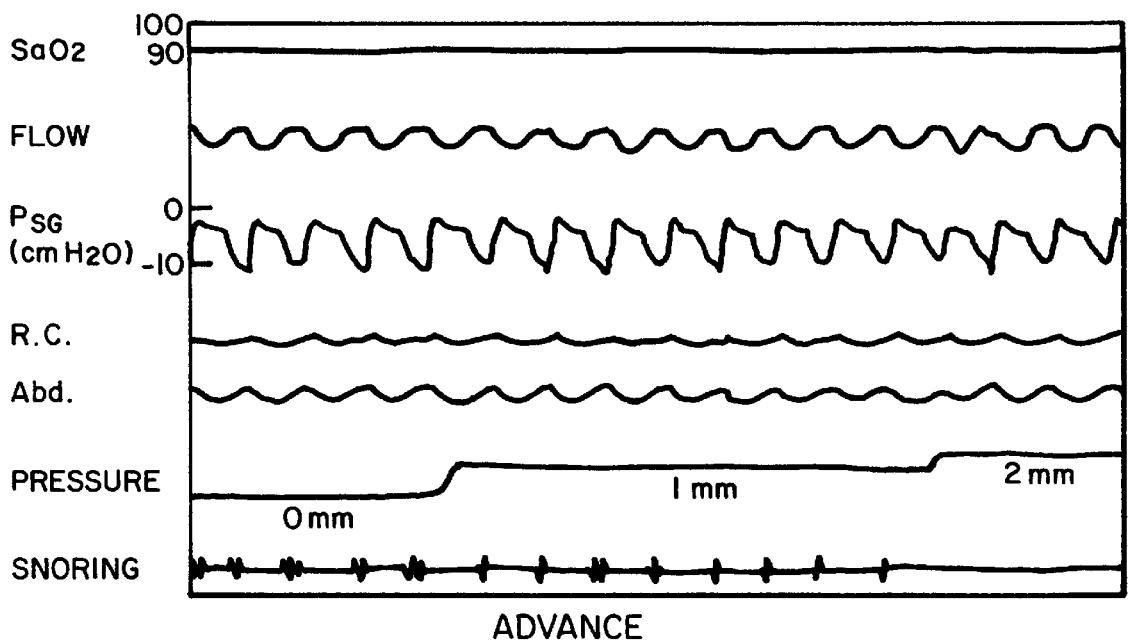
FIG_14A
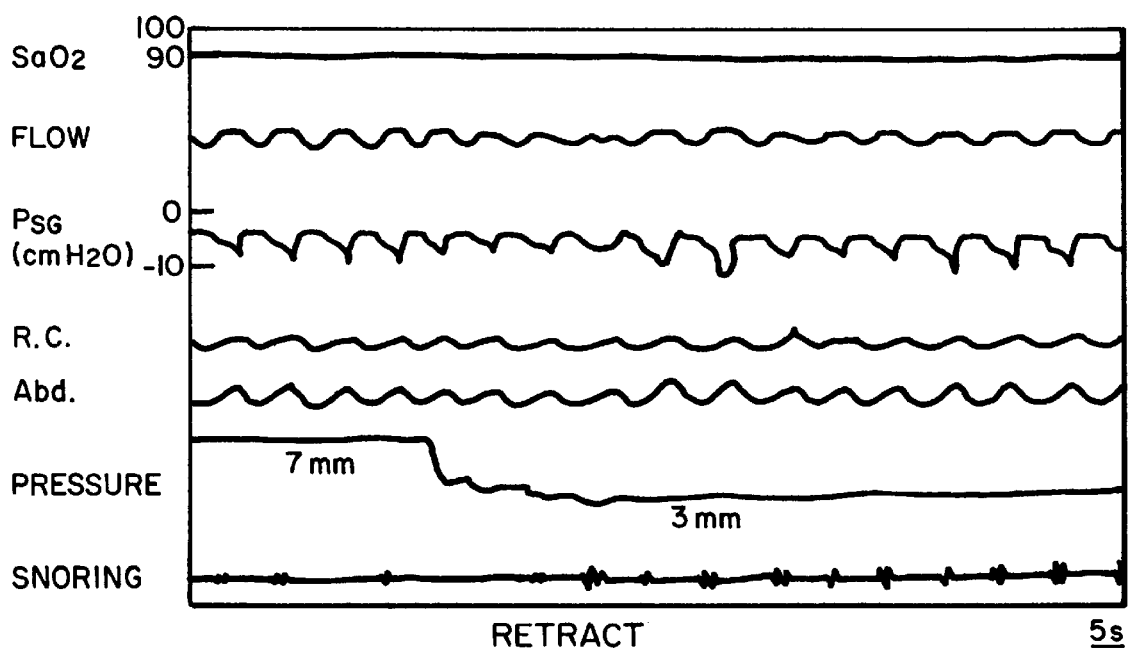
FIG_14B

REMOTE-CONTROLLED MANDIBULAR POSITIONING DEVICE AND METHOD OF USING THE DEVICE

This application claims the benefit of U.S. Provisional Application No. 60/007,155, filed Nov. 1, 1995 and incorporates herein the disclosure of that application in its entirety.

FIELD OF THE INVENTION

The present invention relates generally to systems and methods for diagnosing and treating obstructive sleep apnea using a mandibular positioning device.

BACKGROUND OF THE INVENTION

Obstructive sleep apnea is a common disorder which can produce morbidity and mortality. The disorder arises during sleep when the victim undergoes repeated cessation of breathing. This cessation results from an obstruction of the throat air passage (i.e., pharynx) due to severe narrowing or a collapse of the throat air passage. Repeated cessation of breathing reduces blood oxygen and disturbs sleep. Reduction in blood oxygen can cause hypertension, heart attacks and strokes. Additionally, sleep disturbances can produce excessive daytime sleepiness, headache, depression, irritability and cognitive impairments.

Medical research over the past decade has produced an approach to treatment of obstructive sleep apnea, known as nasal continuous positive airway pressure (i.e., CPAP). In this therapeutic approach, a patient's nose is covered with a mask that forms a pressure seal with the surrounding face. While the patient sleeps, the mask is pressurized to a level that distends the collapsible throat air passage, thereby preventing obstruction.

While there is a continuing need for CPAP technologies, clinical studies and general clinical experience indicate that nasal CPAP is not always an effective treatment for many patients with obstructive sleep apnea, particularly those with symptoms of mild to moderate severity.

Various surgical approaches have been employed to correct the structural abnormality of the pharyngeal airway. Excluding massive reconstruction of the mandibula, maxilla and/or tongue, the only widely employed surgery has been uvulopalatopharyngoplasty (UPPP). However, results with UPPP are disappointing unless patients are selected by pharyngeal endoscopy during sleep and, even then, the long term benefits are questionable. Laser-assisted uvulopalatoplasty (LAUP) is a new approach which has been recommended for obstructive sleep apnea. No studies have reported the effectiveness of LAUP in the treatment of obstructive sleep apnea, but there is little reason to anticipate that it will be more effective than UPPP although it may be more convenient, less expensive and may prove to be a useful adjunct therapy to be used in combination with mandibular positioner (MP) therapy for patients in which MP therapy does not eliminate apneas and hypopneas.

Stationary oral appliances which draw the tongue forward have been used in the treatment of snoring. In addition, some recent studies suggest that a fixed oral appliance (i.e., mandibular positioner) which holds the lower jaw (i.e., mandible) of the patient forward as the patient sleeps is effective in treating obstructive sleep apnea, especially mild obstructive sleep apnea. Studies have shown that ventral displacement of the mandible enlarges the pharyngeal airway and acts to prevent its closure. Conventional mandibular positioners are constructed by a dentist or orthodontist at a fixed position for holding the mandible forward. The proper fixed position is determined through trial and error by having the patient try a series of mandibular positioning devices until the most effective one is found.

An adjustable mandibular positioner, developed by Dr. A. Lowe, Head, Department of Orthodontics, University of British Columbia, allows incremental adjustment of the ventral displacement of the mandible. This device is referred to as a screw adjustable MP (SAMP), because its upper and lower full arch orthotics are connected by a manual screw device which is adjusted by the patient or dentist to set the magnitude of mandibular advancement. Thus, the patient or dentist can progressively advance the mandible with the SAMP over a period of weeks to months so that mandibular muscles and ligaments can adjust, thereby allowing greater ventral displacement and minimizing side effects.

No method is currently available for selecting favorable mandibular positioner therapy candidates in advance of constructing or purchasing a mandibular positioner or SAMP, therefore some patients pay approximately $1,000 for a custom-fitted MP or SAMP and undergo several months of trials or progressive SAMP adjustment without achieving adequate therapy. Second, there is currently no efficient method of determining the extent of mandibular advancement required for therapeutic success in any particular patient in advance of constructing or purchasing a MP or SAMP. Current practice dictates that the dentist, using a MP or SAMP, progressively advances the mandible until snoring, as reported by the bed partner, is eliminated and the patient has a favorable symptomatic response.

Accordingly, it would be desirable to render the diagnosis and treatment of obstructive sleep apnea with a mandibular positioner more practical, convenient and inexpensive. To achieve this end, a convenient and effective method and system for establishing the desired mandible advancement is needed. More particularly, a system is needed which will allow an orthodontist or dentist, following diagnosis with convenient monitoring technology, to prescribe and produce a mandibular positioner which effectively treats obstructive sleep apnea.

SUMMARY OF INVENTION

The present invention is therefore directed to providing a practical, convenient and cost-effective system for identifying candidates suitable for treatment of obstructive sleep apnea with a mandibular positioner, and if a candidate is suitable, identifying the degree of mandibular displacement required for effective treatment.

With respect to the present invention, a remote-controlled mandibular positioner is provided to conveniently and precisely position the mandible during sleep center or in-hospital studies of patients who are candidates for MP therapy. The remote-controlled mandibular positioner is used during sleep. The system of the present invention allows a sleep center to perform a therapeutic titration study during full polysomnographic monitoring. During the titration study, the mandible is advanced by a technician using the remote-controlled mandibular positioner until all apneas and hypopneas are eliminated. The titration study conducted in accordance with the present invention determines whether a mandibular positioner will be effective in treating a particular patient and if so, the degree of mandibular ventral displacement required for effective treatment of obstructive sleep apnea.

In one aspect of the present invention, there is provided a method for determining mandibular displacement effective in treating obstructive sleep apnea in a patient by providing the patient with an adjustable mandibular displacement device, detecting evidence of obstruction of the patient's airway, and displacing the patient's mandible with the adjustable mandibular displacement device until the evidence of obstruction of the patient's airway is reduced or eliminated.

In another aspect of the present invention, there is provided a method for determining mandibular displacement effective in treating obstructive sleep apnea in a patient by (a) providing the patient with an adjustable mandibular displacement device, (b) detecting evidence of obstruction of the patient's airway, (c) displacing the patient's mandible ventrally with the adjustable mandibular displacement device, and (d) repeating steps (b) and (c) until the evidence of obstruction of the patient's airway is reduced or eliminated.

In another aspect of the present invention, there is provided a system for determining whether mandibular displacement is effective in treating obstructive sleep apnea in a patient having an adjustable mandibular displacement device, a unit which detects evidence of obstruction of the patient's airway, and a remote control system associated with the adjustable mandibular displacement device.

BRIEF DESCRIPTION OF THE DRAWINGS

Other objects and advantages of the present invention will become more apparent from the following detailed description of preferred embodiments when read in conjunction with the accompanying drawings, wherein like elements have been designated by like numerals and wherein:

FIG. 1 is a diagrammatic representation of one embodiment of a remote-controlled mandibular positioner system;

FIG. 2 is a user interface in accordance with one embodiment of the present invention for use with the system represented in FIG. 1;

FIG. 3 is a diagrammatic representation of another embodiment of the remote-controlled mandibular positioner system;

FIG. 4 is a board layout of the main control unit circuit board;

FIG. 5 is a schematic of the central processing unit;

FIG. 6 is a schematic of the memory circuitry;

FIG. 7 is a schematic of the power circuitry;

FIG. 8 is a schematic of the display circuitry;

FIG. 9 is a schematic of the mandibular positioner driver circuitry;

FIG. 10 is a schematic of the digital-to-analog converter circuitry;

FIG. 11 is a schematic of the interface circuitry for the main control unit;

FIGS. 12 and 13 are a user interface in accordance with another embodiment of the present invention; and FIG. 14 is a composite of representative polygraphic tracings recorded during a mandibular positioner titration study.

DETAILED DESCRIPTION OF THE PREFERRED EMBODIMENTS

With continued reference to the figures, in particular FIG. 1, there is shown a remote-controlled mandibular positioner system 20 in accordance with one embodiment of the present invention. In this embodiment, adjustable mandibular displacement device 22 comprises a lower dental appliance 24 attached to mounting bracket 26 having a linear actuator 28 mounted thereon. Linear actuator 28 is in contact with or attached to upper dental appliance 30. The upper and lower dental appliances are free to slide relative to each other such that when the linear actuator 28 exerts force on the upper dental appliance (which can not move because the patient's upper teeth are attached to the maxilla which is fixed to the skull) the linear actuator 28, mounting bracket 26 and lower dental appliance 24 are displaced in a direction away from the patient. The lower dental appliance 24 draws the patient's mandible forward (i.e., ventrally) to open the patient's upper airway. In the illustrated embodiment, the actuator 28 and mounting bracket 26 displace the mandible in a linear manner, however it is within the scope of the invention that the actuator and mounting bracket be configured to displace the mandible along the patient's naturally occurring protruding path. For example, the path may be an arcuate path forward and downward, or forward and upward. Likewise, the patient's mandible may angle slightly to one side or the other as it protrudes.

In one embodiment, the upper and lower dental appliances are formed by filling an upper dental tray and a lower dental tray, which can be custom fitted to a particular patient or be in standard sizes, for example small, medium and large, with a silastic molding material (e.g., PolyFil® Trans-Bite available from SciCan® Medtech AG, Cham, Switzerland). Inserting the upper and lower dental trays in the patient's mouth and having the patient bite down until the molding material sets. In other embodiments, the upper and lower dental appliances can be formed with conventional materials such as heat deformable plastics which are placed in heated water or other suitable heating device before being inserted in the patient's mouth.

As illustrated in FIG. 1, the linear actuator 28 is driven by an actuator controller 32 having an external power source 34 (or an internal power source). Actuator controller 32 is controlled by personal computer 36. Personal computer 36 is usually located in an area remote from the patient and the mandibular positioning device 22 such as in a separate room in which an operator or technician provides inputs to the personal computer. Attached to the personal computer 36 is a recording and display device 38 (e.g., a polygraph paper chart and/or a magnetic recording device with a display) which receives inputs from the personal computer 36 and from patient monitoring devices 40 (e.g., standard polysomnograph recording) as will be described in more detail below. The linear actuator 28 can be any of a variety of actuators as will be recognized by one of ordinary skill in the art and be within the scope of the present invention. Two of such actuators are described below. The linear actuator is capable of a maximum displacement of 25 millimeters, but for most patient's the maximum displacement is 16 millimeters.

In one such embodiment, the actuator system is comprised of a stepper motor controller connected to a personal computer for driving a stepper motor connected to a micrometer which moves a first hydraulic piston. The first hydraulic piston is in fluid communication through a 0.5 millimeter inside diameter, 2 millimeter outside diameter hydraulic line with a second hydraulic piston and cylinder mounted on the mounting bracket 26. The second hydraulic piston has a pressure plate for contacting or attaching to the upper dental appliance. When the stepper motor and micrometer move the first hydraulic piston, the pressure in the hydraulic line causes the second hydraulic piston to exert force on the patient's upper teeth through the pressure plate in contact with the upper dental appliance and protrude the patient's mandible with the lower dental appliance. When the pressure in the first hydraulic piston is reduced, the natural elastic nature of the patient's muscles in the jaw cause the patient's mandible to retrude while biasing members attached between the second hydraulic piston and the pressure plate cause the second hydraulic piston to retract. In this embodiment, moving the stepping motor 1 millimeter results in 1 millimeter of displacement of the patient's mandible. Optionally, a pressure transducer can be in fluid communication with the hydraulic line to measure the amount of force being exerted on the patient's muscles and ligaments to prevent excessive force that may cause patient discomfort or arousal. Preferably, the second piston and cylinder and mounting bracket are made of aluminum or similar lightweight material so that the patient is not aware of external forces applied to the patient's teeth.

In another embodiment of the actuator system, the hydraulic system just described is replaced with a small stepper motor (e.g., model no. 20841-05 available from Haydon Switch and Instrument, Inc. in Waterbury, Conn.) mounted on the mounting bracket 26. The actuator controller 32 is a model 40105 Bipolar Chopper Driver available from Haydon Switch and Instrument, Inc. in Waterbury, Conn. The stepper motor mounted on the mounting bracket 26 has a screw shaft extending through the center thereof with a pressure plate at the distal end of the shaft for contacting or attaching to the upper dental appliance. When the actuator controller 32 receives a protrude signal from the personal computer 36, the actuator controller sends a signal to the stepper motor which rotates the screw shaft. The screw shaft extends toward the upper dental appliance to exert force on the patient's upper teeth through the pressure plate in contact with the upper dental appliance and protrude the patient's mandible with the lower dental appliance. When the actuator controller 32 receives a retract signal from the personal computer, the actuator controller sends a signal to the stepper motor which rotates the screw shaft in the opposite direction. The screw shaft retracts the pressure plate and the natural elastic nature of the patient's muscles in the jaw cause the patient's mandible to retrude. In this embodiment, the personal computer sends three signals to the actuator controller. One signal tells the stepping motor to turn on or off, another signal tells the stepping motor the direction to move (i.e., clockwise or counterclockwise), and another signal tells the stepping motor the number of steps to move (e.g., 1 step=15 degrees of shaft rotation=1/40 millimeter of linear displacement).

As shown in FIG. 2, a simple user interface operating in a Windows® environment on the personal computer 36 can be used by a sleep technician remotely operate the adjustable mandibular positioning device 22. The patient's mandible is protruded or allowed to retrude when the technician clicks the Advance or Retract button on the computer screen. The patient's mandible is displaced in discrete steps (e.g., 0.25 millimeter, 0.5 millimeter, 1.0 millimeter, or 2.0 millimeters which can be altered on the computer screen) at a preselected velocity between 0.1 millimeters/second to instantaneous, preferably in the range between 0.1 millimeters/second to 2 millimeters/second. The incremental length of the horizontal bar 42 denotes the absolute position of the linear actuator relative to a fully retruded position (i.e., the position where the patient fully retrudes their jaw such that the T-M joint is fully engaged) up to a fully extended position (i.e., 25 millimeters). In addition, the display 44 displays digitally the piston position, in millimeters, relative to the fully retruded position. The system is set to zero by clicking on the Zero button at the beginning of the study when the pressure plate contacts the upper dental appliance with the patient's mouth closed and the T-M joint fully engaged.

In another embodiment of the remote-controlled mandibular positioner system 20 (FIG. 3), the actuator controller 32 and the logic of the program which was in the personal computer 36 are incorporated into main unit 46 which sits on the table next to the patient's bed. Main unit 46 can use an external power supply 48 or an internal power supply. On the front of main unit 46 is a display 50 showing the current position, in millimeters, of the actuator 28, the step increment, in millimeters, and the step rate (i.e., velocity), in millimeters/second, along with buttons to advance or retract the actuator, change the step increment, step rate, display light intensity and zero the system. Also on the front of the main unit 46 is a connector 51 for sending signals to the actuator 28. The main unit is connected to a remote unit 52 (FIG.3) or personal computer (shown in FIG. 1) in a remote room. The remote unit 52 or personal computer sends signals to the main unit 46 by the bed telling it to advance or retract the actuator. In this embodiment the software is in the main unit by the bed. The remote unit or personal computer is used as a dumb terminal.

The main unit 46 contains the logic and drive circuitry which drives the actuator 28 that moves the lower jaw forward. The remote control unit 52 is located in the technicians room and is connected to the main unit 46 via a serial cable. Remote control 52 uses an external power supply 54 or an internal power supply. The front of the remote unit 52 is similar to the main unit 46 except that the remote unit has no connector for the actuator 28. The remote unit in the illustrated embodiment of FIG. 3 has no motor movement capabilities, instead it allows the user to remotely access the controls of the main unit. The remote unit 52 can be replaced by a personal computer having a serial port and a terminal program. The terminal program which is part of Windows® is an example of a suitable program. Using a personal computer gives the technician all of the capabilities of the remote unit plus extra options as will be described in more detail below.

The main unit 46 is placed next to the patient's head, the connector 51 in the front of the unit accepts a cable from the actuator 28. The rear of the main unit 46 accepts a 24 volt plug from power supply 48 and a serial connection (e.g., a six pin RJ-11 telephone connector) (not shown) which connects the main unit 46 to remote unit 52 or a personal computer. Also on the rear of the main unit 46 is a mini-phono jack which provides an analog signal output to the recording and displaying device 38 representing the current position of the actuator 28. The analog signal output is 100 millivolts for every 1 millimeter advancement (i.e., 0 volts at 0 millimeters and 2 volts at 20 millimeters).

The display 50 has a back lit 16 character 2 line liquid crystal display. The display 50 has four intensity levels, from being off to full brightness, allowing the dimming of the display if it is bothersome to the patient yet allowing the technician to view the display. On the top line of the display the location of actuator 28 is displayed in millimeters. On the second line the step increment (i.e., how many millimeters the mandible will be displaced when the technician presses the PROTRUDE button) is displayed. Also on the second line the step rate is displayed, indicating how many millimeters per second the mandible will be displaced when the technician presses the PROTRUDE button.

On the front of the main unit 46 there are 6 buttons. The PROTRUDE and RETRACT buttons displace the mandible the amount indicated by the current step increment. The STEP INCREMENT button toggles through four values (e.g., 0.25, 0.5, 1.0, and 2.0 mm). The STEP RATE button toggles through the four values (e.g., 0.1, 0.5, 1.0, and 2.0 mm/second). The ZERO button when depressed sets the current position of the actuators as zero. The ZERO button is held down for three seconds before the unit responds to avoid any accidental changing of the current location. The LIGHT INTENSITY button toggles through the four different intensities described above. When any of the buttons is depressed the microprocessor sounds a buzzer to give the technician feedback.

The main unit 46 has a circuit board 58 (FIG. 4) containing a microprocessor based logic circuit and driver system illustrated in FIGS. 4–11. The system is powered by a 24 volt DC power supply for operating the actuator driver circuitry. However, the rest of the system operates at a standard 5 volts through a step down switching regulator built around an LM2575 switching regulator which is designated U1.

The core of the logic circuitry is an MC68HC11 microprocessor designated U3 and address decoding logic components U2, U20, U32, U33, and U35. The microprocessor U3 uses random access memory U15 and the microprocessor software is encoded on the programmable memory chip U8. These components provide the base computer system that accesses and controls the following set of peripheral devices.

One peripheral device is the stepper motor (i.e., actuator) drive circuitry which consists of a stepper motor control chip U9 and driver chip U10 (FIGS. 4 and 9). To drive the stepper motor, the microprocessor provides direction and clocking signals but it is the function of the stepper motor control chip to generate phase information to the driver chip that drives the windings of the stepper motor. The microprocessor can adjust the current that is being delivered to the windings. The current can be reduced from the maximum current which delivers the maximum force to a lower current which provides smoother movement.

Peripheral devices for user interface include a connection to an LCD module designated LM4 and shown in FIG. 8, a speaker designated SPK1 and shown in FIG. 8, and a 6 wire connection P8 to a small front panel circuit board with push buttons (FIG. 11). The microprocessor has a built in serial interface which connects through a MAX232 driver chip designated U5 to connector U6 (FIGS. 4 and 5). The serial interface U6 connects to a personal computer or to the remote control unit 52. An analog indication of motor position is generated using the AD7528 digital to analog converter designated U53 (FIGS. 4 and 10). Other peripheral devices include a DS 1285 clock chip designated U30 (FIG. 8) and a bank of memory for data logging. The data logging memory consist of components U11, U12, and memory chips U38 through U45 (FIGS. 4 and 6).

The primary function of the embedded software of the main unit 46 is to provide an interface to enter high level command to the stepper motor and to translate those commands into direction and clock signals to the stepper motor control chip. The interface is provided in three ways. The first is through the buttons and LCD display on the front panel of the main unit 46. The second is through the serial port to an ANSI based terminal program on a host computer. The third, as an alternative to the second, is through the serial port to a remote control unit 52. In each case high level commands of shaft movement in millimeters are translated into stepper motor drive commands and the progress of motor movement is indicated on the respective display.

The remote control unit 52 is located in the technicians room and is connected to the main unit 50 through the serial connection. The front of the remote unit is similar to the front of the main unit and the same information is displayed on the remote unit display 56 as is displayed on the display 50 of the main unit 46. An optional piece of information shown on the remote display is the intensity of the main unit's back lit display. The actions of the buttons on the remote are the same as the actions described previously with respect to the main unit. There is no connector on the front of the remote unit for connection to the actuator as the remote unit does not have the capability to drive the actuator, only the ability to send control signals to the main unit. The rear of the remote unit is similar to the rear of the main unit having an output of the current position as an analog signal and having a serial connector. The power supply 54 is 12 volts DC while the main unit power supply 48 is 24 volts DC.

A personal computer as described with respect to FIG. 1 can be used in place of the remote control unit 52. The serial cable from the main unit 46 that connects to the remote unit 52 can be connected into the serial connector of a personal computer using an adapter. Any terminal communication software package on the personal computer can be used to control the main unit using the personal computer. For example, the terminal program shown in FIGS. 12 and 13. The serial setting on the personal computer is set to 8 bits, no parity, stop bit and 9600 baud. Using the menus that are displayed on the terminal screen, the main control unit can be controlled from the computer. The computer can also be used to customize the default values in the main control unit, such as changing the toggle values available for the step increments and the step rate. For example, the toggle values for the step increment could be changed from 0.25. 0.5, 1.0. 2.0 to 0.1, 0.25. 0.75, 1.5.

To perform a titration study utilizing the remote-controlled mandibular positioning system of the present invention to determine whether a patient is a good candidate for a mandibular positioning device, and if so, what the optimum mandibular displacement is for effectively treating sleep apnea, the patient is instrumented as usual for the standard polysomnograph recording. This includes electro-encephalogram (EEG), electro-oculogram (EOG), submental electromyogram (EMG), electrocardiogram (ECG), arterial oxygen saturation ($0_2$ sat), volume excursion of the rib cage and abdomen, snoring sound and body position. These signals are recorded on a polygraph (and/or magnetic recording media) and displayed to a sleep technician. In addition, an index of respiratory airflow is recorded with nasal prongs which record pressure in the nasal airstream and supraglottic pressure through a water-filled catheter positioned in the supraglottic space. The amount of mandibular displacement is shown on the polygraph as a DC voltage value with 100 millivolts representing each 1 mm advancement (i.e., 0 volts=0 mm; 2 volts=2 mm). See FIG. 14. It is not required that all of these characteristics be recorded and evaluated to perform the titration study. Any one of these characteristics or combinations of characteristics can be used to perform the evaluation.

After this instrumentation, an upper and a lower dental appliance are created for the patient. These are temporary appliances which are made by the sleep technician and are for use during the sleep study. This entails filling an upper tray (which can be a partial or full arch) and a full arch lower tray with silastic impression material. The upper and lower trays are simultaneously inserted into the mouth and the patient. The patient bites down and holds the occluded position for 0.5 to 2 minutes. After the material is set, the upper and lower dental trays are removed and excess impression material is removed. The actuator is attached to the strut of the lower appliance. The upper and lower appliances are repositioned in the patient's mouth.

The patient retrudes their mandible to a fully retruded position while the pressure plate of the actuator is brought into contact with the upper appliance. The position of the lower appliance at this point is referred to as zero. The patient then assumes the normal rest position of the mandible and the pressure plate is again brought into contact with the upper appliance and this position is recorded relative to the zero (i.e., fully retruded) position.

The patient is allowed to go to sleep or induced to sleep while the device is at a normal rest position. When evidence of obstruction of the upper airway (e.g., snoring, hypopneas or apnea) is detected, the mandible is protruded a predetermined step (e.g., 0.5 mm) at a predetermined velocity (e.g., 0.1 mm/sec). After each protrusion displacement, the changes in the evidence of obstruction (e.g., airflow pressure) are observed by the technician for 1 to 2 minutes. The usual pattern is that evidence of upper airway obstruction disappears (e.g., airflow increases and/or pressure fluctuations decrease) immediately after the mandible is protruded and, over a period of 10–30 seconds, evidence of upper airway obstruction reappears. If evidence of upper airway obstruction reappears, the mandible is again advanced a predetermined step as previously described. This step-wise process of advancement and monitoring of upper airway obstruction continues until all evidence of upper airway obstruction is eliminated. The protrusive distance is then noted and the procedure is repeated with the patient in another body position or in another stage of sleep. The titration study establishes the protrusive distance which relieves all evidence of upper airway obstruction in rapid eye movement sleep state and non-rapid eye movement sleep state with the patient supine and in a lateral decubitus posture.

The protrusive distance effective in eliminating evidence of upper airway obstruction is then provided to a dentist or orthodontist for constructing a mandibular positioner for the patient. Alternatively, the upper appliance and lower appliance can be clamped together when the effective displacement is reached and sent to the dentist or orthodontist for constructing the mandibular positioner. If evidence of an obstructed airway is never eliminated, then it is established that the patient is not a candidate for mandibular positioner therapy.

The remote-controlled mandibular positioner system of the present invention has been used in experimental studies of patients with moderate or severe obstructive sleep apnea. The results for a patient who was evaluated during natural sleep is described herein. The patient is a 30 year old male with severe obstructive sleep apnea (i.e., respiratory disturbance index of 120/hr; respiratory disturbance index is the number of apneas and hypopneas occurring per hour) who had mild to moderate daytime somnolence.

FIG. 14 provides a composite of representative polygraphic tracings recorded during the remote-controlled mandibular positioner titration study on this patient. With the mandible at the zero position (i.e., full retrusion of the mandible and complete engagement of the T-M joint), the patient experienced repetitive apneas and hypopneas associated with large respiratory fluctuations of supraglottic pressure ($P_{SG}$) (not shown). Part A of FIG. 14 shows that displacing the mandible from the zero position 1 millimeter and then 1 more millimeter to a position of 2 millimeters eliminated snoring, decreased the respiratory fluctuations in $P_{SG}$ and increased $SaO_2$. Progressive advancement of the mandible eliminated all respiratory disturbances and progressively reduced the negative swing in $P_{SG}$, indicative of decreasing pharyngeal resistance. At a position of 9 mm, the patient exhibited only occasional snoring and respiratory disturbances. Conversely, retrusion of the mandible caused reappearance of snoring, increase in respiratory fluctuations of $P_{SG}$ and a decrease in $SaO_2$, as shown in part B of FIG. 14.

It will be appreciated by those of ordinary skill in the art that the present invention can be embodied in other specific forms without departing from the spirit or essential character thereof. The presently disclosed embodiments are therefore considered in all respects to be illustrative and not restrictive. The scope of the invention is indicated by the appended claims rather than the foregoing description, and all changes which come within the meaning and range of equivalents thereof are intended to be embraced therein.

What is claimed is:

1. A method for determining mandibular displacement effective in treating obstructive sleep apnea in a sleeping patient, comprising:

providing the patient with a remotely-controlled adjustable mandibular displacement device;

detecting evidence of obstruction of the sleeping patient's airway; and displacing the sleeping patient's mandible while the patient is asleep with a remote unit which sends a signal to a first unit which relays a signal to the remotely-controlled adjustable mandibular displacement device until the evidence of obstruction of the sleeping patient's airway is reduced below a predetermined value or eliminated.

2. The method of claim 1 wherein the detecting step further comprises:

detecting respiratory variation, apnea and hypoventilation.

3. The method of claim 1 wherein the detecting step comprises:

monitoring oxygen saturation, nasal airflow or snoring sound.

4. The method of claim 1 wherein the detecting step comprises:

monitoring supraglottic pressure and respiratory airflow.

5. The method of claim 1 wherein the detecting step comprises:

monitoring pressure, airflow, sound, oxygen saturation and body position.

6. The method of claim 1 further comprising:

recording the amount of mandibular displacement that is effective in reducing or eliminating the evidence of obstruction of the patient's airway.

7. The method of claim 1 further comprising:

recording the amount of mandibular displacement that is effective in reducing or eliminating the evidence of obstruction of the sleeping patient's airway when the sleeping patient is in a non-rapid eye movement sleep state, in a rapid eye movement sleep state, in a supine position, and in a lateral decubitus posture.

8. The method of claim 1 further comprising:

recording the amount of mandibular displacement that is effective in reducing or eliminating the evidence of obstruction of the sleeping patient's airway when the sleeping patient is in a non-rapid eye movement sleep state or in a rapid eye movement sleep state.

9. The method of claim 8 wherein the recording step further comprises:

recording the amount of mandibular displacement that is effective in reducing or eliminating the evidence of obstruction of the sleeping patient's airway when the sleeping patient is on their side or in a lateral decubitus posture.

10. A method for determining mandibular displacement effective in treating obstructive sleep apnea in a sleeping patient, comprising the steps of:
(a) providing the patient with a remotely-controlled adjustable mandibular displacement device; (b) detecting evidence of obstruction of the sleeping patient's airway;
(c) displacing the sleeping patient's mandible ventrally while the patient is asleep with a remote unit which sends a signal to a first unit which relays a signal to the remotely-controlled adjustable mandibular displacement device; and
(d) repeating steps (b) and (c) until the evidence of obstruction of the sleeping patient's airway is reduced below a predetermined value or eliminated.

11. The method of claim 10 wherein step (a) comprises:
filling an upper and a lower dental tray with molding material;
inserting the upper and lower dental trays into the patient's mouth while the patient is awake until the molding material sets to form an upper dental appliance and a lower dental appliance;
attaching an actuator to the lower dental appliance; and
repositioning the upper and the lower dental appliances in the patient's mouth while the patient is awake.

12. The method of claim 11 further comprising:
attaching the upper and the lower dental appliances together at a position effective in eliminating the evidence of obstruction of the sleeping patient's airway.

13. The method of claim 12 further comprising:
forming a mandibular positioner for the patient.

14. The method of claim 10 wherein step (b) comprises:
monitoring changes in airflow, snoring and supraglottic pressure.

15. The method of claim 10 wherein step (c) comprises:
protruding the patient's mandible a predetermined distance if evidence of obstruction of the patient's airway is detected.

16. The method of claim 10 wherein step (c) comprises:
protruding the patient's mandible a predetermined distance at a predetermined velocity if evidence of obstruction of the sleeping patient's airway is detected.

17. The method of claim 16 wherein the predetermined distance is in the range of 0.25 to 2 millimeters.

18. The method of claim 16 wherein the predetermined velocity is in the range of 0.1 to 2 millimeters/second.

19. The method of claim 10 wherein when step (d) is performed step (b) is performed for a duration of about 1 minute.

20. The method of claim 10 further comprising:
recording the amount of mandibular displacement that is effective in reducing or eliminating the evidence of obstruction of the sleeping patient's airway when the sleeping patient is in a supine position.

21. The method of claim 10 further comprising:
recording the amount of mandibular displacement that is effective in reducing or eliminating the evidence of obstruction of the sleeping patient's airway when the sleeping patient is in a lateral decubitus posture.

22. The method of claim 10 further comprising:
recording the amount of mandibular displacement that is effective in reducing or eliminating the evidence of obstruction of the sleeping patient's airway when the sleeping patient is in a non-rapid eye movement sleep state.

23. The method of claim 10 further comprising:
recording the amount of mandibular displacement that is effective in reducing or eliminating the evidence of obstruction of the sleeping patient's airway when the sleeping patient is in a rapid eye movement sleep state.

24. A system for determining mandibular displacement effective in treating obstructive sleep apnea in a sleeping patient, comprising:
an adjustable mandibular displacement device;
a unit which detects evidence of obstruction of the sleeping patient's airway;
a remote control system used to displace the adjustable mandibular displacement device while the patient is asleep, the remote control system comprising a first unit which sends signals to protrude the adjustable mandibular displacement device; and
a remote unit which sends signals to the first unit to protrude the adjustable mandibular displacement device.

25. The system of claim 24 wherein the adjustable mandibular displacement device comprises:
an upper dental appliance;
a lower dental appliance having a mounting bracket extending therefrom; and
an actuator attached to the mounting bracket and in contact with the upper dental appliance.

26. The system of claim 24 wherein the control system comprises:
a first unit which sends signals to protrude the adjustable mandibular displacement device; and
a remote unit which sends signals to the first unit to protrude the adjustable mandibular displacement device.

27. The system of claim 24 wherein the remote unit is a personal computer.

28. The system of claim 24 wherein the remote unit is a personal computer with a mandibular displacement device controller.

29. The system of claim 24 wherein the first unit has mandibular displacement device controller circuitry and logic which protrudes the adjustable mandibular displacement device.

30. The system of claim 29 wherein the first unit comprises:
a display which displays the current location and step increment of the adjustable mandibular displacement device;
a first input device which displaces the adjustable mandibular displacement device; and
a second input device which adjusts the step increment.

31. The system of claim 30 wherein the remote unit comprises:
a display which displays the current location and step increment of the adjustable mandibular displacement device;
a first input device which sends signals to the first input device of the first unit; and
a second input device which sends signals to the second input device of the first unit.

* * * * *